(12) United States Patent
Rührnschopf et al.

(10) Patent No.: US 7,822,172 B2
(45) Date of Patent: Oct. 26, 2010

(54) METHOD FOR HARDENING CORRECTION IN MEDICAL IMAGING

(75) Inventors: Ernst-Peter Rührnschopf, Erlangen (DE); Bernhard Scholz, Heroldsbach (DE)

(73) Assignee: Siemens Aktiengesellschaft, Munich (DE)

(*) Notice: Subject to any disclaimer, the term of this patent is extended or adjusted under 35 U.S.C. 154(b) by 571 days.

(21) Appl. No.: 11/973,471

(22) Filed: Oct. 9, 2007

(65) Prior Publication Data

US 2008/0095302 A1     Apr. 24, 2008

(30) Foreign Application Priority Data

Oct. 13, 2006   (DE) .................. 10 2006 048 626

(51) Int. Cl.
*A61B 6/03* (2006.01)
(52) U.S. Cl. ............................. 378/19; 378/4
(58) Field of Classification Search ............. 378/4, 378/5, 18, 19, 207
See application file for complete search history.

(56) References Cited

U.S. PATENT DOCUMENTS

| | | | | |
|---|---|---|---|---|
| 5,243,664 | A * | 9/1993 | Tuy | 382/130 |
| 6,094,467 | A * | 7/2000 | Gayer et al. | 378/4 |
| 2006/0109949 | A1* | 5/2006 | Tkaczyk et al. | 378/4 |
| 2006/0159223 | A1* | 7/2006 | Wu et al. | 378/18 |

FOREIGN PATENT DOCUMENTS

DE      100 51 462 A2     4/2002

OTHER PUBLICATIONS

Tuy, A post-processing algorithm to reduce metallic clip artifacts in CT images, 1993, European Radiology, vol. 3, pp. 129-134.*
G.T. Herman, S.S. Trivedi, "A Comparative Study of Two Postreconstruction Beam Hardening Correction Methods", IEEE Transactions on Medical Imaging, Sep. 1983, pp. 128-135., vol. MI-2, No. 3.
Peter M. Joseph; Robin D. Spital, "A Method for Correcting Bone Induced Artifacts in Computed Tomography Scanners", Journal of Computer Assisted Tomography, Jan. 1978, pp. 100-108, vol. 2.
J. Hsieh, R.C. Molthen, C.A. Dawson; R.H. Johnson, "An interative approach to the beam hardening correction in cone beam CT", Medical Physics, Jan. 2000, pp. 23-29, vol. 27, No. 1.
M. Zellerhoff, B. Scholz, E.-P. Rührnschopf, T. Brunner, "Low contrast 3D reconstruction from C-arm data", Proceedings of SPie, Medical Imaging 2005, pp. 646-655, vol. 5745.

(Continued)

*Primary Examiner*—Edward J Glick
*Assistant Examiner*—John M Corbett

(57) ABSTRACT

The invention relates to a method for beam hardening correction in medical image. Beam hardening within the context of medical imaging projection image profiles are split up into a basic profile which is assigned to a homogeneous object area and into a detailed profile which is assigned to an inhomogeneous object area. On the basis of the basic profile and of the difference profile the mass occupancy of the different components in the object to be examined can be approximately determined. On the basis of the approximately determined mass occupancy the correction of the beam hardening can then be performed directly on the projection data.

20 Claims, 7 Drawing Sheets

OTHER PUBLICATIONS

D.M. Lewis, P.C. Chatwin, "The treatment of atmospheric dispersion data in the presence of noise and baseline drift", Boundary-Layer Meteorology, Jan. 1995, pp. 53-85, vol. 72, Nos. 1-2.

Peter M. Joseph, Christopher Ruth, "A Method for Simultaneous Correction of Spectrum Hardening Artifacts in CT Images containing both Bone and Iodine", Medical Physics, Oct. 1997, pp. 1629-1634, vol. 24, No. 10.

William H. Press, Brian P. Flannery, Saul A. Teukolsky, William T. Vetterling, "Numerical Recipes—The Art of Scientific Computing/ (FORTRAN Version)", 1989, pp. 268-273, The Press Syndicate of the University of Cambridge, Cambridge.

E.P.Rührnschopf, W.A. Kalender, "Artefacts Caused by Non-Linear Partial-Volume and SPectral Hardening Effects in Computerized Tomography", Siemens Aktiengesellschaft Medical Engineering Group, Electromedica 2, 1981, pp. 96-105.

* cited by examiner

METHOD FOR HARDENING CORRECTION IN MEDICAL IMAGING

CROSS REFERENCE TO RELATED APPLICATIONS

This application claims priority of German application No. 10 2006 048 626.9 filed Oct. 13, 2006, which is incorporated by reference herein in its entirety.

FIELD OF THE INVENTION

The invention relates to a method for hardening correction in medical imaging.

BACKGROUND OF THE INVENTION

A method of this type is known from DE 100 51 462 A1. The known method involves a method for correction of the beam hardening for images which have been recorded within the framework of computer tomography.

Computer tomography (CT) is an established imaging method of x-ray diagnostics. The latest CT systems are multilayer CT, spiral CT and conebeam CT with flat-panel detector. The x-ray radiation required for computer tomography is created for current devices with the aid of x-ray tubes. The radiation of x-ray tubes is polychromatic. The consequences of this are as follows:

During the penetration of material the lower-energy photons are attenuated more strongly than the photons of higher energy, which leads to a material-dependent and wavelength-dependent beam hardening. The result is a dominance of photons of higher energies in the spectrum. This phenomenon even occurs with objects made of homogeneous material. For the penetration of a cylindrical body filled with water transverse to the longitudinal axis the hardening for rays at the edge is less than for rays in the middle of the cylinder which travel a long way through the body.

The theory of CT reconstruction algorithms requires monochromatic radiation. If the polychromasy is ignored the reconstruction leads to what is known as a cupping effect: the reconstructed attenuation coefficient (gray value) decreases continuously from the edge inwards. This effect is relatively easy to correct for so-called water-equivalent materials of a low ordinal number, such as soft tissue, fat and many plastics. The correction is undertaken in such cases within the context of a so-called water correction or 1st-order hardening correction.

Above and beyond this the beam hardening is increased by the presence of materials of higher ordinal number, above all for contrast media, but also for bones or with metal implants. Even after previous water correction local density faults still occur after the reconstruction, especially dark bars or shadow-type artefacts, for example between or in the extension of contrast media-filled vessels or heavily-absorbent bone structures. Such 2nd-order hardening artefacts can in extreme cases reach a strength of more than around 100 HU (1 HU=1 Hounsfield Unit). The 2nd-order hardening artefacts can adversely affect diagnosis. For example the risk arises of false positive findings of pseudo-stenoses which are apparent constrictions in what are actually normal vessels, or the detectability of smaller lesions in cases of density caused by hardening is rendered more difficult. The cause of the 2nd-order artefacts is the energy dependence of the attenuation coefficients which differ greatly from water in materials with a higher ordinal number.

Water-equivalent materials are also referred to below as W-materials and materials with a higher ordinal number, for example contrast media, implants or bones, as K-materials. Correction methods require knowledge of which of the individual measured values have been influenced by the transmission through K-material and how many of these the respective measurement rays have penetrated.

The known correction method obtains the knowledge from a first image or volume reconstruction about which of the individual measured values have been influenced by transmission through K-material and how much K-material the respective measurement ray has penetrated. Subsequently a segmentation of the reconstructed volume is conducted with a separation into two components, namely W-material and K-material generally being undertaken with the aid of a threshold criterion. By a subsequent reprojection, in which the individual measurement rays are traced back through the volume, it can be approximately determined which material lengths the individual measurement rays have traveled through W-material and through K-material respectively. After the hardening correction at least one second reconstruction is necessary, with further iteration steps able to follow. This type of correction method is often also referred to as bone correction.

On account of the reprojection and the second reconstruction such correction methods are complex.

A direct method for correction of the projection data would be desirable, so that the expensive iteration with reprojection and second reconstruction can be avoided.

SUMMARY OF THE INVENTION

Using this prior art as its starting point, the underlying object of the invention is thus to specify a method for correction of the beam hardening which can be executed solely on the basis of the projection images.

This object is achieved by a method with the features of the independent claim. Advantageous embodiments and developments are specified in its dependent claims.

The method comprises the following steps:
an object to be examined is irradiated with the aid of a radiographic source,
the radiation which has passed through the object is detected by a radiation detector, and
the projection images are corrected in respect of beam hardening by an evaluation unit connected downstream from the radiation detector.

In the method a projection image profile is initially divided up by the evaluation unit into a basic profile and a detailed profile. Subsequently the projection image profile is segmented by the evaluation unit on the basis of predetermined characteristics of the detailed profile into profile sections. In a profile section which is assigned to a homogeneous object area formed by a basic component of the object, the mass occupancy of the basic components is determined and a one-component correction of the beam hardening is performed. In a profile section which is assigned to an object area formed from the basic component and a further detailed component of the object, the mass occupancy of the basic components and the detailed components based on the basic profile and the projection image profile is determined and subsequently a multi-component correction of the beam hardening is performed. The method makes use of the fact that objects to be examined in the medical field frequently largely consist of a basic component with detailed components embedded in it. A basic profile adapted to an image profile is thus essentially determined by the mass occupancy of the basic components.

This also applies in those areas of the projection image in which a composition of basic components and detailed components is responsible for the image values. The basic component thus contains information about the mass occupancy of the basic component whereas the detailed profile contains information about the mass occupancy of the detailed component. The evaluation of the separate information can be used to perform a hardening correction even on the projection image.

In one embodiment of the method, in which the detailed component mixes with the basic component, the mass occupancy of the basic component is determined with reference to the basic profile and the mass occupancy of the detailed component with the aid of the known mass occupancy of the basic component with reference to the project image profile. Typical applications for this embodiment of the method are methods for medical imaging, in which parts of the soft tissue of a patient are filled with contrast media.

In a further embodiment of the method, in which the detailed component replaces the basic component in the object to be examined, the total of the mass occupancies of basic component and detailed component is determined with reference to the basic profile. Subsequently the mass occupancies of the detailed component and of the basic component are determined using the known total of the mass occupancies from the projection image profile. This embodiment is an obvious choice if, within the framework of medical imaging areas in the projection images are to be corrected in respect of beam hardening, which map embedded bone tissue or implants in soft tissue.

Preferably the basic profile is determined by adapting an adaptation curve to the projection image profile. Since the basic profile reproduces the low-frequency components of the projection image profile, it can be assumed that with the aid of this type of adaptation curve, the wide-area distribution of the basic component of the object can be determined.

The detailed profile is preferably equal to the difference curve between the basic profile and the projection image profile. In this way the detailed profile contains the higher-frequency components of the projection image profile and can be included for determining the distribution of the detailed component in the object to be examined.

To eliminate the influence of noise in the projection image profile, when the projection image profile is segmented, those sections in which the detailed profile exceeds predetermined threshold values are assigned to a composition of basic component and detailed component.

Since a radiation detector with a plurality of detector elements arranged alongside each other is preferably used for the radiation detector, by which one pixel of the pixel image is recorded in each case, the projection image profile will preferably be examined along a row of detector elements.

The method for correction of the beam hardening is especially suitable for medical imaging methods in which a plurality of projection images must be processed. This is the case for example with medical imaging methods in which a plurality of projection images of the object to be examined have to be recorded from different projection directions.

Preferably the method is used within the framework of computer tomography. The radiographic source in such cases is preferably an x-ray radiation source while an x-ray detector is used as the radiation detector.

BRIEF DESCRIPTION OF THE DRAWINGS

Further advantages and details of the invention emerge from the description below, in which exemplary embodiments of the invention are explained in detail with reference to the enclosed drawing. The figures show:

FIG. 18 a reconstructed cross-sectional view of the phantom from FIG. 5 when poly-energetic x-radiation is used if hardening correction is dispensed with;

DETAILED DESCRIPTION OF THE INVENTION

Figure 1:
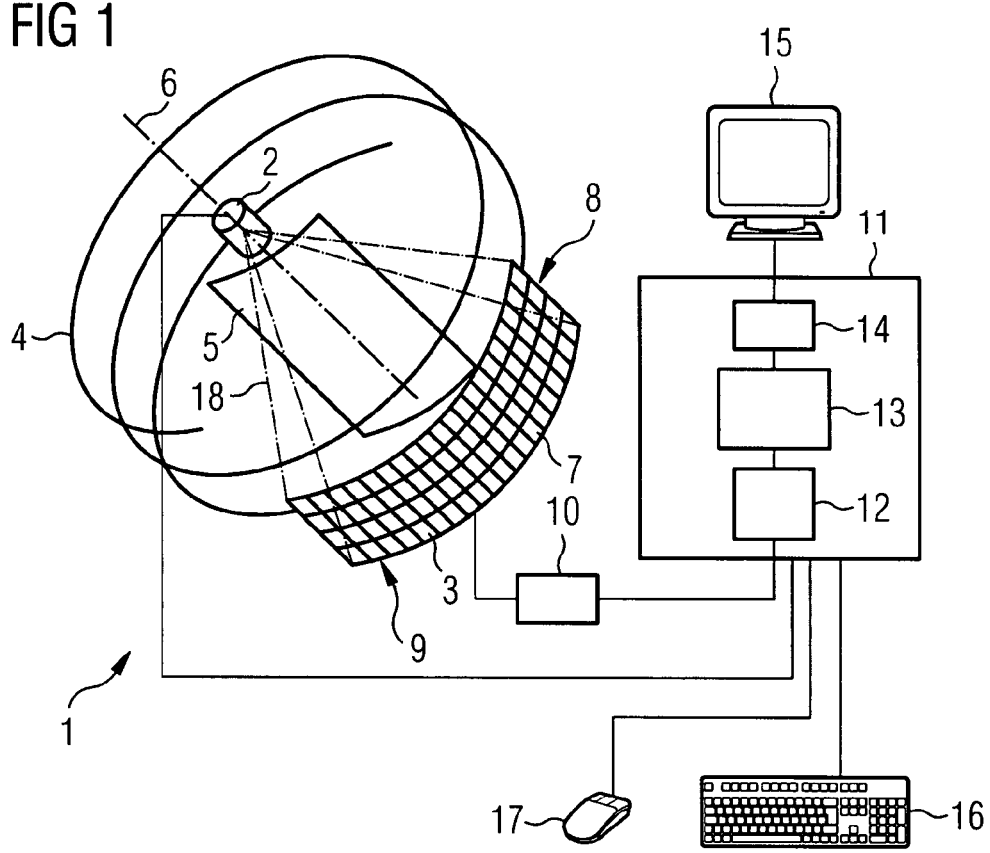
FIG. 1 a computer tomography device.

FIG. 1 shows a computer tomography device 1 which features an x-ray tube 2. The x-ray tubes 2 and the x-ray detectors 3 move on a track 4 around a patient support table 5, on which a patient not shown in FIG. 1 is located during the examination. Usually the x-ray detector 3 and the x-ray tubes 2 are guided by a yoke and run in the yoke on a circular path around the patient support table 5. The yoke and the patient support table 5 can move relative to one another along a longitudinal axis 6. The track 4 is in this case spiral-shaped in relation to the patient support table 5.

The x-ray detector 3 is preferably a digital flat-panel detector which is made up of a plurality of detector elements 7, the so-called pixels. The detector elements 7 are preferably arranged in rows 8 and columns 9. Furthermore a readout circuit 10 and also an evaluation circuit 10 are connected downstream from the x-ray detector 3. The evaluation unit 11 can for example be a commercially-available computer. The evaluation unit 11 includes a correction module 12 which makes image corrections to the image data recorded at the x-ray detector 3. The correction module 12 is followed by a reconstruction module 13, which creates from the projection images a two-dimensional cross-sectional image or three-dimensional volume images of the examined patient. The reconstruction module 13 can be followed by an image processing module 14 in which the cross-sectional images or volume images delivered by the reconstruction module 13 are prepared for viewing on a monitor 15.

The x-ray tubes 2 are also controlled by the evaluation unit 11. Also connected to the evaluation unit 11 are input devices, such as a keyboard 16 or a mouse 17, with which the evaluation unit 11 and thereby the computer tomography device 1 can be controlled.

The x-ray detector 3 detects the x-ray radiation emitted by the x-ray tubes 2 corresponding to a beam of radiation 18. Accordingly projection images are recorded of the patient located on the patient support table 5. For the reconstruction of a volume image or of a cross-sectional image it is necessary to record projection images of the patient from a plurality of projection directions.

Since a plurality of projection images must be processed by the computer tomography device 1, it is of advantage for the hardening correction to already be able to be undertaken on the basis of the projection images. A method is therefore described in detail below for performing the hardening correction on the basis of the projection images.

1. Beam Hardening

The energy spectrum of the photons emitted as braking radiation from the anode of the x-ray tubes 2 depends on the high voltage U applied, with which the electrons are accelerated from the cathode to the anode. The maximum photon energy is then $E_{max}(U)=U(keV/kV)=eU$ with the energy unit kiloelectronvolts [keV].

Figure 2:
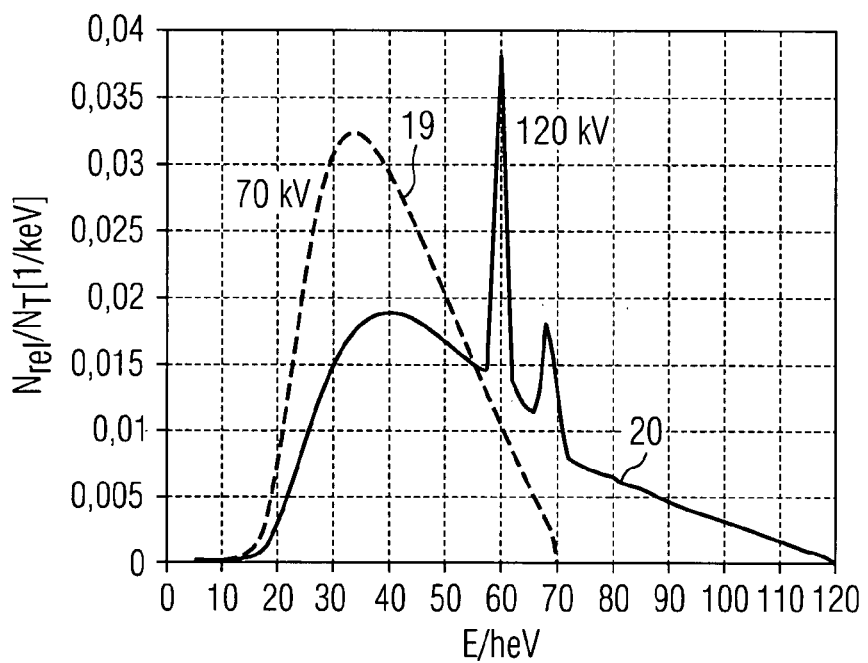
FIG. 2 Typical emission spectra of an x-ray tube with a tungsten anode.

FIG. 2 shows typical emission spectra 19 and 20 for a tube voltage of U=70 kV and 120 kV respectively. The relative photon frequency $N_{rel}$ pro keV interval in relation to the total number NT of the photons contained in the overall emission spectra 19 and 20 is plotted in FIG. 2.

For imaging however the emission spectrum $Q_E(U)$ is not the sole deciding factor, but also the transparency $W(E)=\exp(-\mu(E)T)$ of the spectral filters used. The spectral filters can be made of aluminum, copper or titanium for example and have an energy-dependent attenuation coefficient $\mu(E)$ and a thickness T. Furthermore the spectral response sensitivity $\eta_D(E)$ of the x-ray detector 3 is to be taken into consideration. The resulting effective normalized spectral distributions are then produced for $$S_U(E)=Q_U(E)W(E)\eta_D(E)/c_U \quad (\#1);$$

with the factor $c_U$ normalizing the integrated effective nominated spectral distribution to the value=1.

Figure 3:
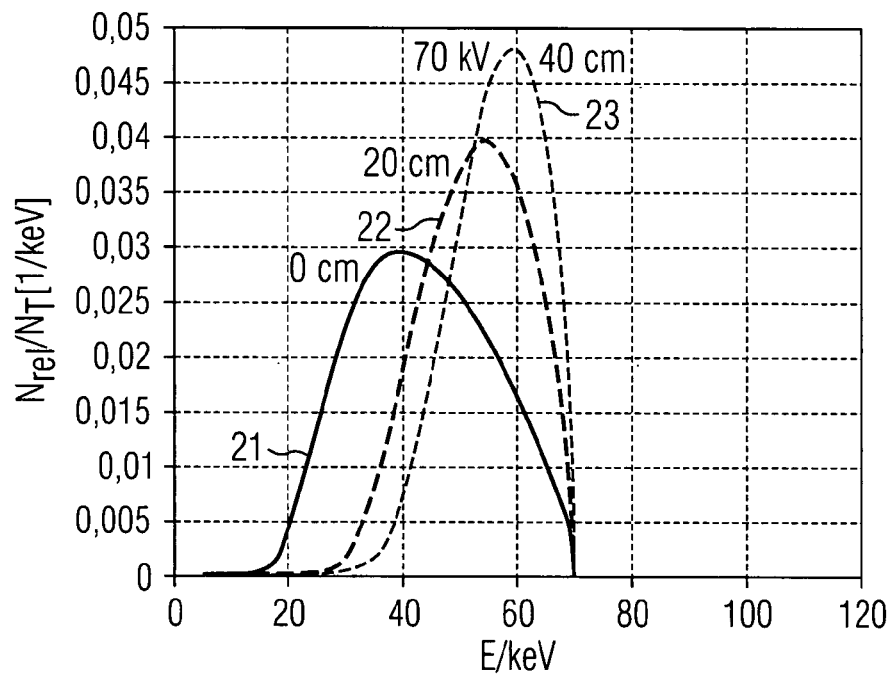
FIG. 3 effective spectral distributions behind water.

On penetration of material the low-energy photons are more heavily attenuated than the high-energy photons, which leads to a material and path-length-dependent hardening because of the dominance of photons of higher energies in the spectrum. As an example FIG. 3 shows spectral distributions 21, 22 and 23 hardened by transmission through 20 and 40 cm of water. In FIG. 3, as in FIG. 2, the relative photon frequencies $N_{rel}$ per 1-keV interval are plotted against the total number of photons NT. It can be seen from FIG. 3 that as the path length through water increases, the frequency of the low-energy photons decreases in relation to the high-energy photons.

Figure 4:
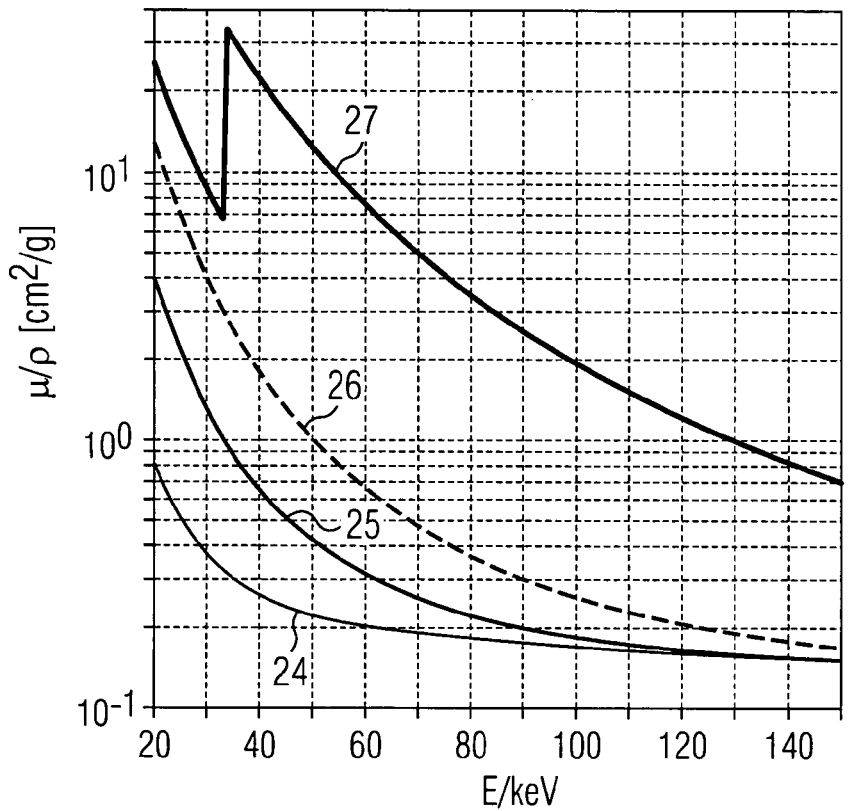
FIG. 4 the dependency of the mass attenuation coefficients of different parts of the body as a function of the energy of the x-ray photons.

This hardening which occurs on passage through material of the spectrum is however not similar for all materials. FIG. 4 shows the dependency of the so-called mass attenuation coefficient $(i/\tilde{n})(E)$ for different typical parts of the body. In FIG. 4 a mass attenuation curve 24 describes the mass attenuation coefficient for soft tissue or water as a function of the photon energy E. Further mass attenuation curves 25, 26 and 27 illustrate the passage of the mass attenuation coefficient for bone tissue, calcium and the typical contrast medium of iodine.

Thus different methods must be applied for the correction of the beam hardening for different materials.

2. Direct 1st-order Beam Hardening Correction

In direct 1st-order beam hardening correction or water correction, it is assumed for the sake of simplicity that the attenuation of an x-ray beam will be solely caused by water-equivalent material. In this case water-equivalent means that the energy dependence of the mass attenuation coefficient $(\mu/\rho)(E)$ is identical to water and that differences are only based on local density differences. To this extent muscle tissue or blood or also bones are treated like water with a higher density $\rho > 1 \text{ g/cm}^3$.

A measurement ray of a radiation beam 18 which penetrates the object will now be considered. The coordinates along its path are designated as x and the local linear energy-dependent attenuation coefficient is $$\mu(x,E)=\rho(x)\alpha(x,E),$$

with the mass attenuation coefficient being abbreviated to $\alpha$: $\alpha(x,E)=\mu(x,E)/\rho(x)$.

The polychromatic logarithmic CT projection value for the measurement ray considered is then $$\tilde{p} = p^{poly} \quad (\#2a)$$
$$= -\ln\left(\int_0^{eU} \exp\left(-\int \mu(x,E)dx\right)S_U(E)dE\right)$$
$$= -\ln\left(\int_0^{eU} \exp\left(-\int \rho(x)\alpha(x,E)dx\right)S_U(E)dE\right)$$

It should be noted that equation (#2a) is a general formulation for any spectral distributions and also applies for the idealized case of a monochromatic spectrum with the discrete energy line E': Then $S_U(E')=\delta_E(E')$ is to be set, with the centered Dirac distribution for $E'=E$ $\delta_E(E')=\delta(E-E')$ and this produces the following result of the associated monochromatic CT projection value for $$p_E^{mono}=\int\mu(x,E')dx=\int\rho(x)\alpha(x,E')dx \quad (\#2b)$$

For equation (#2a) an equivalent water thickness $b=b(\tilde{p})$ is determined in the following way:

$\alpha$Let $_W(E)$ be the energy-dependent mass attenuation coefficient of water. The polychromatic logarithmic projection value for a measurement ray with the voltage-dependent spectral distribution $S_U(E)$, which is attenuated along a path length of occupancy thickness b in water ($\rho=1 \text{ g/cm}^3$), can be determined for $$f_W(b) = -\ln\left(\int_0^{eU} \exp(-b\alpha_W(E))S_U(E)dE\right) \quad (\#3)$$

This function can be calculated in advance for any voltage U or also defined experimentally. Since the function increases monotonously with b, the function can be at least numerically inverted. In particular for each polychromatic measured value $\tilde{p}$ according to equation (#2a) an equivalent water thickness $\tilde{b}=b(\tilde{p})$ can be defined so that $\tilde{p}=f_W(\tilde{b})$ in accordance with equation (#3) applies, namely through inversion of equation $$\tilde{b} = f_W^{-1}(\tilde{p}) \quad (\#4)$$

With $\tilde{b}$ it is then possible to convert to the corresponding projection value, which would have ideally been measured for monochromatic radiation with photons of only one single reference energy $E_0$: With $\tilde{b}$ in accordance with equation (#4) the corrected water-equivalent monochromatic logarithmic projection value is produced $$p^{korr(0)} = p_{E_0}^{mono} = \alpha_W(E_0)\tilde{b} = \alpha_W(E_0)f_W^{-1}(\tilde{p}) \quad (\#5)$$

It should be pointed out that the right-hand sides of the equations (#2a) and (#3) are identical if the measurement ray penetrates an occupancy thickness b in water: Then in equation (#2) $b=\int\rho(x)dx$ and $\alpha(x,E)=\alpha_W(E)$.

3. 2nd-order Component-selective Hardening Correction

With known mass occupancies of the individual materials a second-order hardening correction can be performed with the aid of a correction table calculated in advance.

For example let a method for material-selective 2nd-order hardening correction be considered in which the influence of two materials with occupancy thicknesses $b_W$ and $b_K$ is taken into account. The index W in this case stands for water-equivalent or soft tissue, the index K, for materials such as contrast media or bones.

The pair of values ($b_W$, $b_K$) is then assigned, by accessing a correction table, a correction factor for conversion of polychromatic projection data which is disturbed by the hardening effect, into monochromatic projection data. If necessary there can be interpolation between the table values.

The multi-parameter correction table C, which is discretized in relation to $b_W$ and $b_K$ in fine steps and which still depends on the tube voltage U, can be calculated in advance in the following manner, possibly also determined or adapted with measurements:

$$C(b_W,b_K) = g_0(b_W,b_K,E_0)/g(b_W,b_K) \quad (\#6)$$

In this case $g_0$ and $g$ are the logarithmized mono- and polychromatic CT projection value $$g_0(b_W,b_K,E_0) = b_W\alpha_W(E_0) + b_K\alpha_K(E_0) \quad (\#7)$$

$$g(b_W, b_K) = -\ln\left(\int_0^{eU} \exp(-b_W\alpha_W(E) - b_K\alpha_K(E))S_U dE\right) \quad (\#8)$$

It should be pointed out that equation (#7) for a monochromatic spectrum with the discrete energy line $E_0$ and $S_U(E_0) = \delta_E(E_0) = \delta(E-E_0)$ is identical to equation (#8)

The comparison of equations (#8) with equation (#3) shows that the following applies $$f_W(b) = g(b,0) \quad (\#9)$$

By contrast with water correction, where the equivalent occupancy thickness for water is calculated by inversion in accordance with equation (#4), the requirement is now for a suitable method for direct determination of the 2-component occupancy thicknesses $b_W$ and $b_K$ to be available. This method will be described in greater detail below.

The hardening correction of the polychromatic measured projection data $\tilde{p}$ is then undertaken multiplicatively with the correction factor C $$p^{korr} = C(b_W,b_K)\tilde{p} \quad (\#10)$$

or additively $$p^{korr} = \tilde{p} + \delta pp \quad (\#11)$$

with $$\delta p = (C(b_W,b_K)-1)\tilde{p} \quad (\#12)$$

4. Pre-reconstructive Component Separation

A projection image profile formed from projection data is considered for component separation. With multi-cell or flat-panel detectors the projection image profile can be examined along a line of the detector.

Initially a base line of the projection image profile is determined, with the assumption being made that the base line is essentially determined by W-material. Subsequently significant local profile increases are determined since it is assumed that they are caused by K-material in the object to be investigated. The method steps are:

Determination of the base line

Determination of a difference profile from the measured projection image profile and the base line Application of a threshold value criterion to the difference profile, to identify the significant profile increases and thereby to obtain the K-material profile.

Obtaining the W-material profile.

4.1 Base Line Determination

The base line is the profile function of the object to be examined were it to consist entirely—even its bone areas—of W-material. After smoothing the data line considered is divided up into an adequate number of intervals of the same size. The interval minima form the set of checkpoints for a curve adaptation. This set of checkpoints can be subjected to further selection criteria in order to optimize the curve adaptation and thereby the determination of the base line. It is for example advantageous to assume that the gradients between the checkpoints decrease monotonously from outside to inside. Points which contribute to the violation of the monotony condition are points in the area of profile peaks or—troughs and are thus not points on the base line. They will thus be removed from the set of checkpoints. The choice of adaptation curve is application-dependent. For example a conical-section curve can be selected for base line determination. The adaptation curve obtained is regarded as the base line.

4.2 Difference Profile

The difference between the measured projection image profile and the base line produces the difference profile. As a result of a non-ideal base line, because of noise and also of thicker W-material in the ray input, the difference profile does not just contain the significant profile peaks.

The significant profile peaks remain in the difference profile if the non-significant proportions are eliminated by means of a threshold value criterion. The threshold value can correspond to a K-material occupancy to be predetermined.

The segmented difference profile is identified below by $p_K(y)$ since it is caused by K-materials in the beam input. The coordinate y specifies the detector pixel location.

From the projection image profile determined by measurement p(y) and the $p_K(y)$ profile just obtained, the profile $p_W(y)$ is obtained by differentiation, which is to be attributed to W-materials (water-equivalent materials or soft tissue) in the ray input. Consequently the following applies:

$$p(y)=p_W(y)+p_K(y) \qquad (\#13)$$

Vessels filled with contrast media are especially suitable for the separation algorithm, since as prominent local maxima of lower width they can be localized just as well as spectral lines in spectrograms. The separation of bone structures is significantly more difficult in practice.

5. 2nd-order Component-selective Direct Hardening Correction

Whereas with conventional methods the occupancy thickness $b_W$, $b_K$ is determined by a reconstruction with subsequent segmentation of the reconstructed volume image, the determination of the occupancy thicknesses here is undertaken solely on the basis of the projection data. In this case a non-linear coupling resulting from the hardening is present in the two components in the projection data. This state of affairs requires a procedure adapted to the respective situation.

Two specific applications—contrast media and bones—are distinguished below, which are to be treated differently.

The following findings apply point-by-point for each detector pixel y. Therefore the local variable y can be left out in the splitting up of equation (#13) below.

5.1 Direct Hardening Correction for Contrast Media: Resolving the Admixture Problem In the following derivation the assumption is made that initially only water-equivalent soft tissue, i.e. W-material, is present. Contrast media is mixed into the blood in the vessels. No W-material is expelled by the contrast media admixture. This does not change the W-material occupancy [g/cm²] $b_W$ along the measurement ray. On successful separation $b_W$ can then be obtained directly from $p_W$ through inversion of the equation $f_w(b_W)=p_W$ $$b_W=f_W^{-1}(p_W) \qquad (\#14a)$$

With this fixed value $b_W$ the equation (#8) is then reduced to a non-linear equation for the unknown $b_K$:

$$g(b_W,b_K)=p \qquad (\#14b),$$

with $p=p_W+p_K$ applying.

The solution this non-linear equation (#14b) can be determined for example with an inverse interpolation or the iterative Newton method.

By solving the equation system (#14a-b) $b_W$ and $b_K$ are obtained. The 2-component hardening correction can then be performed in accordance with equation (#7).

It should be pointed out that a component separation is also obtained in $p_W$ and $p_K$ with the subtraction angiography method, which however requires two recordings, a mask image logarithmized under some circumstances $p_W$, possibly without contrast media, and a filling image logarithmized under some circumstances $p=p_W+p_K$, possibly with contrast media.

5.2 Direct Hardening Correction for Bones: Resolving the Replacement Problem If the hardening correction is performed in the presence of bones, the situation is somewhat different: Each point of the separated basic curve $p_W(y)$ corresponds to a fully water-equivalent geometrical path length b in the object. Where there is bone, water-equivalent W-material will be replaced by bone. Accordingly the path length of the W-material is reduced by the path length of the W-material $b_K$ so that then: $b_W=b-b_K$.

Given a known density however the path length of the K-material can be uniquely determined.

For the determination of the two unknowns $b_W$, $b_K$ we therefore have a non-linear system of two equations:

$$f_w(b_W+b_K)=p_W \qquad (\#15a)$$

$$g(b_W,b_K)=p \qquad (\#15b).$$

The inverse of the function $f_w$ in (#15a) corresponds to the water correction, which means that (#15a) can be linearized by inversion. If we introduce the following abbreviation $$b=f_W^{-1}(p_W) \qquad (\#16a),$$

the equation (#15b) then reduces to $$g(b-b_K,b_K)=p \qquad (\#16b),$$

This is a non-linear equation for only one unknown $b_K$. In this case $$b_W=b-b_K \qquad (\#16c).$$

By solving (#16a-c) one thus obtains $b_W$ and $b_K$. This then enables the 2-component hardening correction to be performed again in accordance with equation (#7).

It should be noted that the variables $b_W$ and $b_K$ here—by contrast with the application of contrast media in the previous section, have the meaning of linear lengths [cm] and that the density of the K-material is taken as known.

5.3 Linear Approximation as Starting Value for the Iterative Solution of the Non-linear Equations The non-linear equations (#14b) and (#16b) can be solved with few iteration steps of the Newton method, provided a good approximation is available for the start of the iteration.

For derivation we consider the equation (#8). The expression in the exponents on the right-hand side of equation (#8) can be transcribed as follows $$b_W\alpha_W(E)+b_K\alpha_K(E)=(b_W+b_K)\alpha_W(E)+b_K(\alpha_K(E)-\alpha_W(E)) \qquad (\#17)$$

Equation (#17) would be identical to equation (#7) in the idealized cases of a monochromatic spectrum with the discrete energy line for E=E'.

The first expression on the right-hand side of equation (#17) represents the water-equivalent attenuation part for photons of the energy E which would be effective if the total path length or mass occupancy along the ray were only to consist of W-material. The first expression thus corresponds to $p_W$ in the resolution into equation (#13) for the case of a monochromatic spectrum.

The second expression on the right-hand side represents the remaining proportion, which is based on the different attenuation properties between K-material (contrast media) and W-material. The second expression thus corresponds to $p_K$ in the resolution in equation (#13). This remaining proportion would disappear if the second material identified by "K" were once again water-equivalent.

Now $b_W$ and $b_K$ are to be estimated for the general case of a polychromatic x-ray spectrum. To this end one considers the resolution into equation (#17) and replaces the attenuation coefficients there by suitable attenuation coefficients averaged over the energy spectrum $<\alpha_W>$ and $<\alpha_K>$, which are to be identified by pointed brackets, so that the following approximation then applies $$p=p_W+p_K=(b_W'+b_K')<\alpha_W>+b_K'(<\alpha_K>-<\alpha_W>) \qquad (\#18).$$

The notation of the material thicknesses $b_W'$, $b_K'$ with single quotation marks ' is intended to indicate that these are approximations:

With equation (#18) the following is obtained as an estimated value for the K-material thickness $$b_K' = \frac{p_K}{<\alpha_K> - <\alpha_W>} \quad (\#19)$$

and with the first expression in (#18): $p_W = (b_W' + b_K') <\alpha_W>$ the following is obtained as an estimated value for the W-material thickness (equivalent water thickness)

$$b_W' = \frac{p_W}{<\alpha_W>} b_K' \quad (\#20)$$

6. Exemplary Embodiments

The various types of hardening correction are illustrated below with reference to a simple example.

Figure 5:
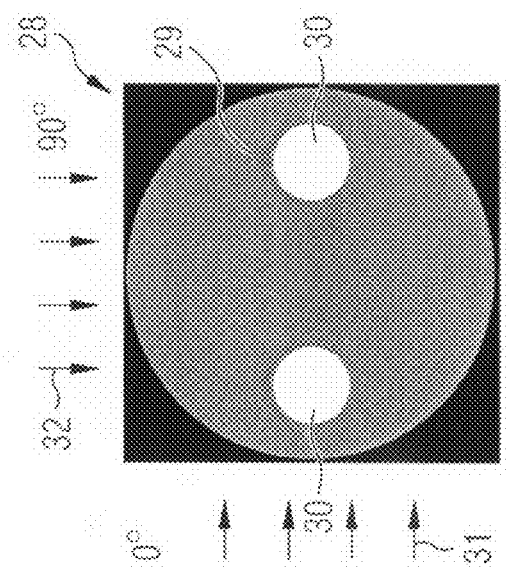
FIG. 5 a cross-sectional view of a phantom from which projection images are created from different projection directions.
Figure 6:
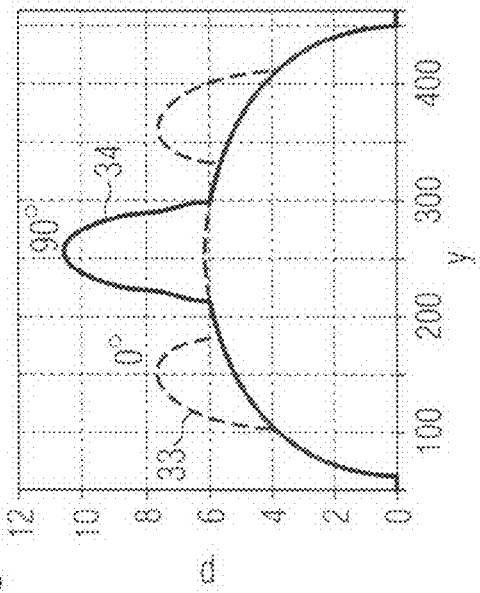
FIG. 6 the projection image profile corresponding to the cross-sectional view from FIG. 5 of projection images taken from different projection directions.
Figure 7:
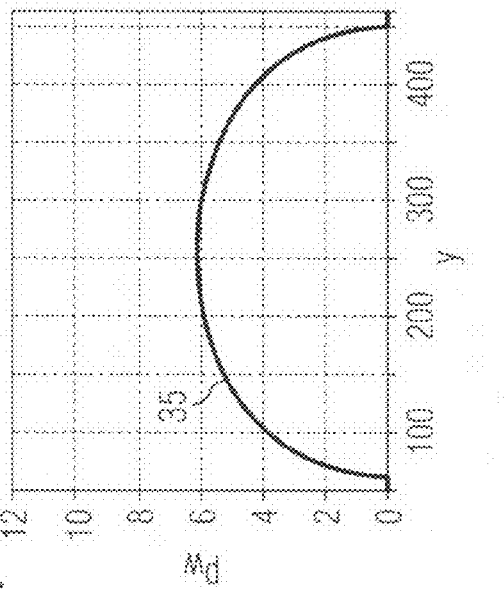
FIG. 7 a base line of the projection image profile from FIG. 6.
Figure 8:
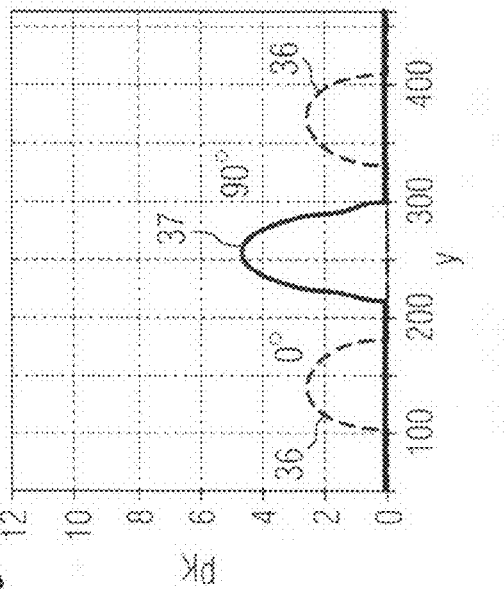
FIG. 8 a diagram of difference profiles of the projection image profile from FIG. 6.

FIG. 5 shows a cross-sectional view of a phantom 28. The phantom 28 depicted in FIG. 5 involves a soft tissue cylinder 29, into which two bone cylinders 30 are embedded. The phantom 28 is irradiated from a first direction of projection 31, to which the projection angle 0° is assigned, and from a second direction of projection to which the projection angle 90° is assigned. In this case the projection image profiles 33 and 34 shown in FIG. 6 are produced. The projection image profiles 33 and 34 can then in accordance with the method explained in detail above, be divided up into a basic profile 35 and the difference profiles 36 and 37 shown in FIG. 8. From the information contained in the basic profile 35 and in the difference profiles 36 and 37, the mass occupancy of the individual components in the body of the patient can then be determined.

6.1 Use of Contrast Media

This involves a non-linear method, as described above. The inverse of the function g in equation (#14b) as function of $b_K$, for fixed parameters $b_W$, can be calculated in advance and stored as a set of tables $h(p; b_W)$ as a function of p for different water thicknesses $b_W$.

6.2 Use of Bone

Here too a non-linear method is involved, as described above. The inverse of the function in equations (#16b) can be calculated in advance and stored as a set of tables as a function of p for different total lengths b.

Figure 9:
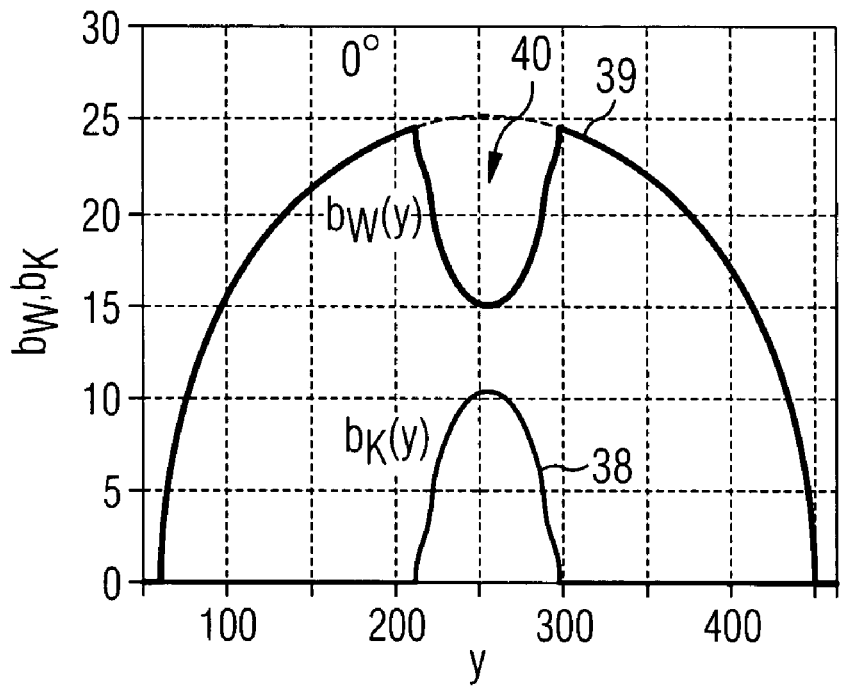
FIG. 9 a diagram of the reconstructed path lengths in the phantom from FIG. 5 when the projection image profile recorded at an angle of projection of 0° is used.

Results of obtaining the path lengths $b_W$ and $b_K$ according to equations (#16a-c) for a simple example, in which the separation of the projection data is exactly possible, are shown in FIG. 9 and results of the image reconstruction before and after the hardening correction described are shown in FIGS. 11 to 14.

FIG. 9 shows a distribution curve 38, which describes the mass occupancy of the two bone cylinders 30 for the direction of projection 31. A further distribution curve 39 shows in FIG. 9 the mass distribution of the soft tissue in the soft tissue cylinder 29 for the direction of projection 31. Since the bone tissue in the bone cylinders 30 replaces the soft tissue in the soft tissue cylinder 29, the distribution curve 39 for soft tissue has a complementary trough 40 to the distribution curve 38 for bone tissue.

Figure 10:
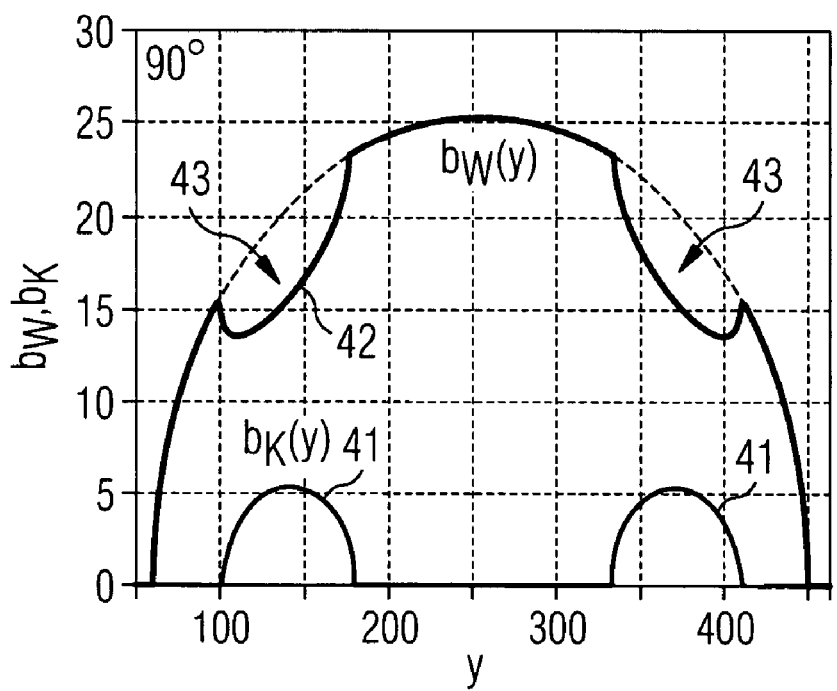
FIG. 10 a diagram of the reconstructed path lengths within the phantom from FIG. 5 when the projection image profile recorded at an angle of projection of 90° is used.

In FIG. 10 a distribution curve 41 shows the mass occupancy in the bone cylinders 30, while a further distribution curve 42 describes the mass occupancies in the soft tissue cylinder 29. In accordance with FIG. 9 the distribution curve 42 has troughs 43 which are complementary to the distribution curve 41.

In FIGS. 9 and 10 the distribution curves 38, 39 as well as 41 and 42 are each plotted against the column index y of the x-ray detector 3.

Figure 11:
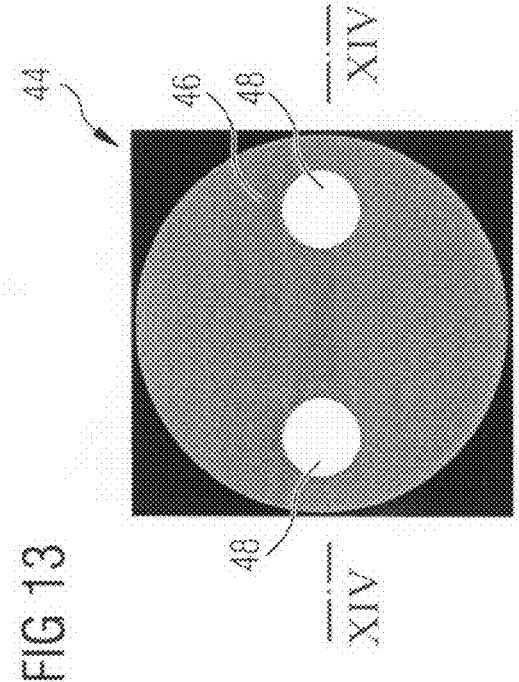
FIG. 11 a reconstructed cross-sectional view without hardening correction.

FIG. 11 shows a reconstructed cross-sectional view 44, which has been created without prior correction of the beam hardening. One feature able to be established in FIG. 11 is an edge brightening 45 at the edge of a reconstructed soft tissue cylinder 46. FIG. 11 also shows typical bar artefacts 47 which occur between two reconstructed small bone cylinders 48 in the soft tissue cylinder. By contrast such second-order artefacts do not occur if the two small cylinders consist of high-density soft-tissue-like plastic such as Teflon for example.

Figure 12:
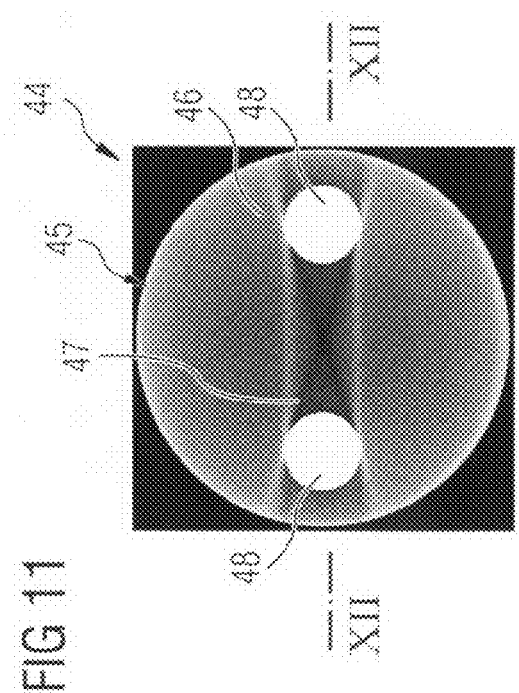
FIG. 12 a cross-sectional profile along the center line XII-XII of the cross-sectional view from FIG. 11.
Figure 14:
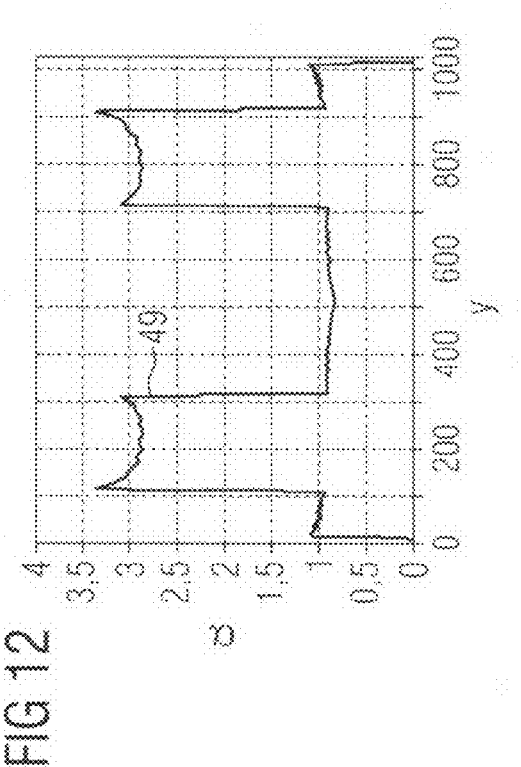
FIG. 14 a cross-sectional profile along the center line XIV-XIV of the cross-sectional view from FIG. 13.

FIG. 12 shows a reconstructed gray level profile 49 along the cutting line XII-XII in FIG. 11. On the basis of FIG. 12 the cupping effect within the reconstructed soft tissue cylinder 46 and the reconstructed bone cylinder 48 can be clearly seen.

Figure 13:
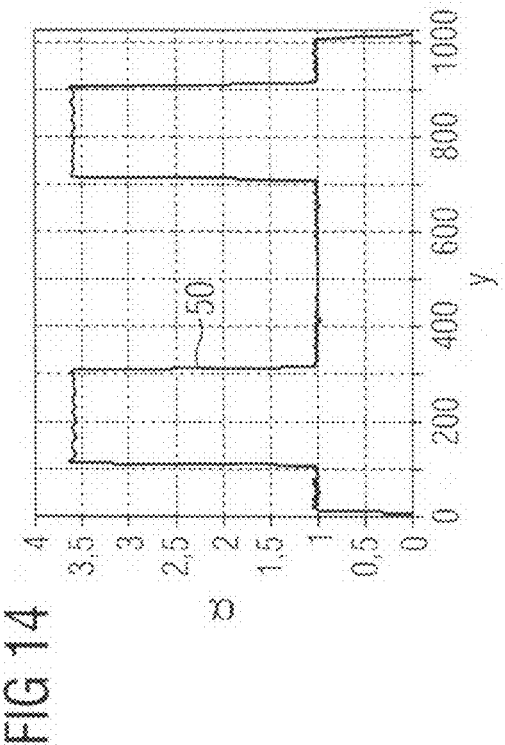
FIG. 13 a reconstructed cross-sectional view with hardening correction.

In FIG. 13 by comparison the reconstructed soft tissue cylinder 46 and the reconstructed bone cylinder 48 are shown for prior scattered radiation correction. In this case no edge brightening 45 and no bar artifacts 47 occur. This is also evident from a gray value profile 50 shown in FIG. 14 which runs along at the cutting line XIV-XIV in FIG. 13.

Figure 15:
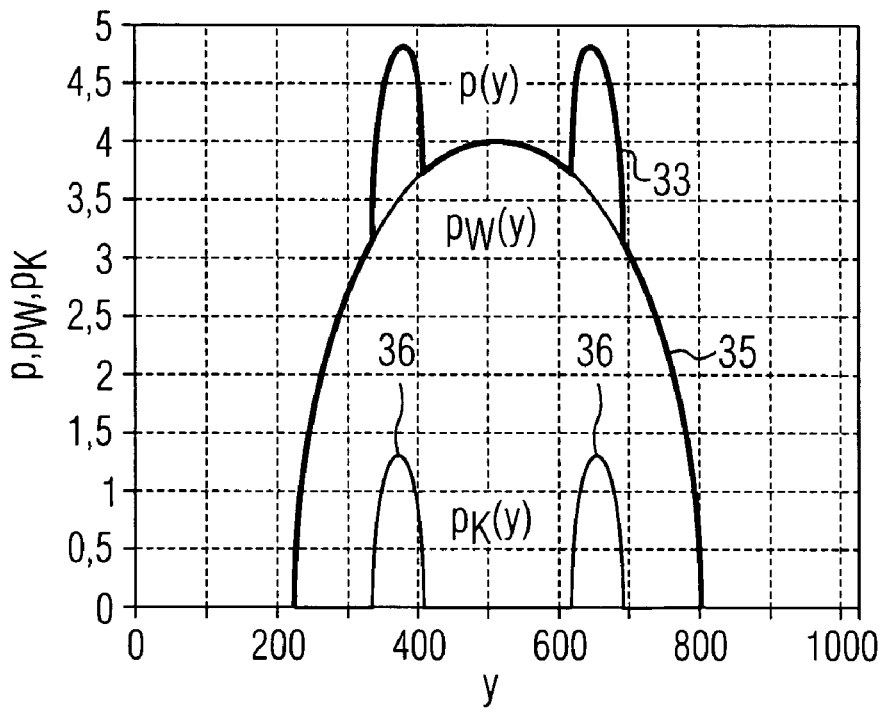
FIG. 15 a diagram which shows the division of a projection image profile into a basic profile and a difference profile.
Figure 16:
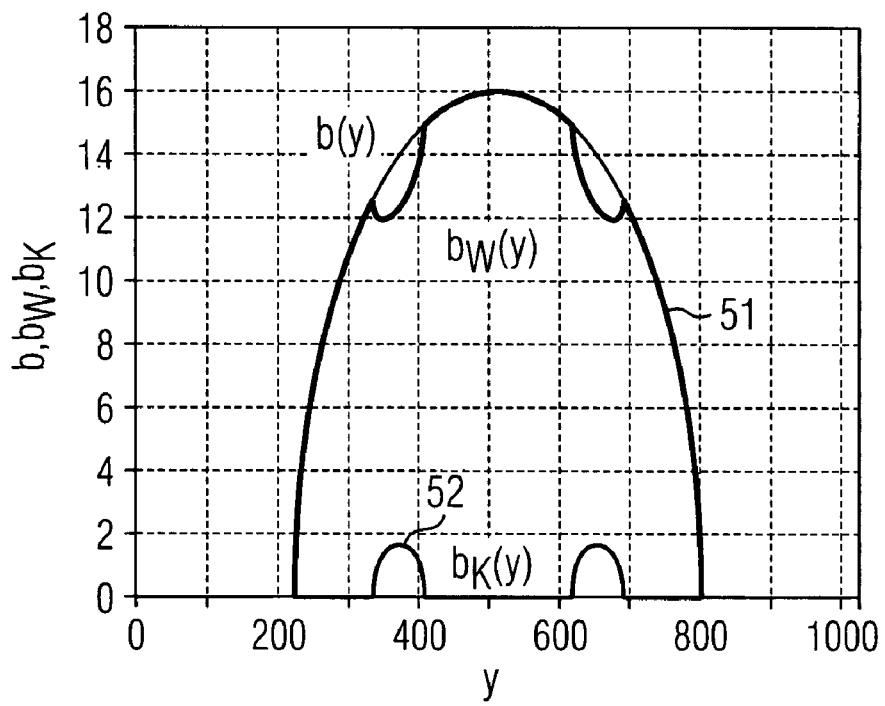
FIG. 16 a diagram which shows the path lengths determined on the basis of the basic profile and the difference profile.

Simulation calculations have also been performed on the basis of the phantom 28. FIG. 15 illustrates, on the basis of simulated poly-energetic projection image data, the segmentation of a projection image profile 33 assigned to projection direction 32 into the basic profile 35 and the difference profile 36. From the basic profile 35 and the difference profile 36 the distribution curves 51 and 52 are produced in accordance with the equations (#19a, b) shown in FIG. 16 for the mass occupancy in the soft tissue cylinder 29 and in the bone cylinders 30.

Figure 17:
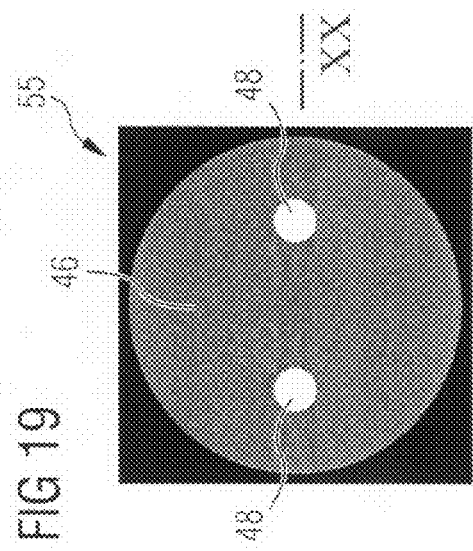
FIG. 17 a cross-sectional view of the phantom from FIG. 5 when mono-energetic x-radiation is used.

To make the effect of the proposed pre-reconstructive correction clear, different reconstruction results are summarized in FIGS. 17 through 20:

A reconstructed cross-sectional view 53 which is shown in FIG. 17 has been produced on the basis of mono-energetic projection image data. In this case no artifacts occur.

Figure 18:
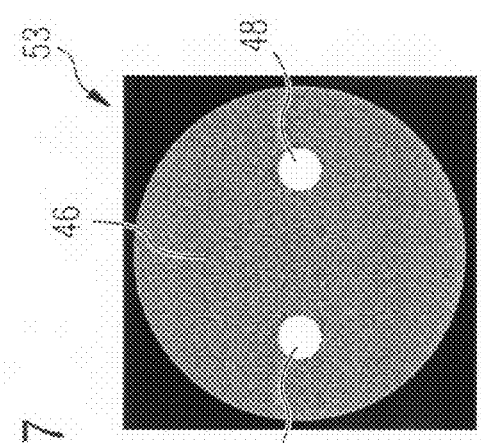

FIG. 18 shows a further reconstructed cross-sectional view 54, a which has been produced on the basis of poly-energetic projection image data without prior hardening correction. In this case the artifacts already explained with a reference to FIG. 11 occur. In particular the edge brightening 45 and the bar artefacts 47 are evident.

Figure 19:
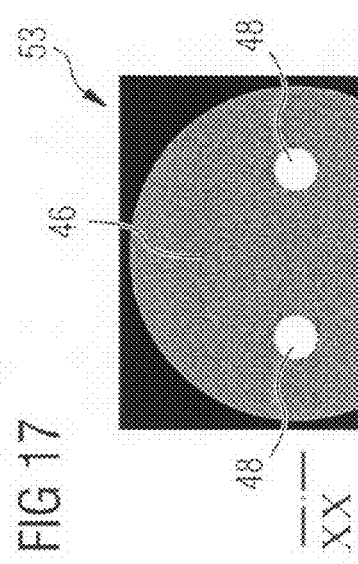
FIG. 19 a reconstructed cross-sectional view of the phantom from FIG. 5 when poly-energetic x-radiation is used after application of a water correction and a bone correction.

FIG. 19 finally shows a reconstructed cross-sectional view 55, which has likewise been created on the basis of poly-energetic projection image data. However in this case the reconstruction has only been performed after a the first-order and second-order correction of the beam hardening has been undertaken. Although the pre-reconstructed combined W- and K-material correction of the projection data, because of the base line lift separation method as expected is not ideal, the water-corrected and bone-corrected image still exhibits a significant improvement of the image quality compared to the uncorrected image.

Figure 20:
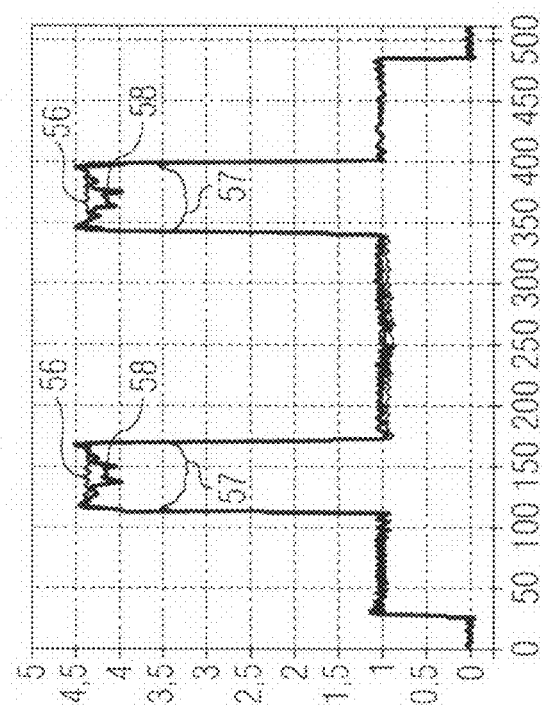
FIG. 20 a diagram in which the cross-sectional profiles are drawn-in along the center line XX-XX through the reconstructed cross-sectional views of FIGS. 17 to 19.

This is also shown by the gray value profile depicted in FIG. 20 along the cutting lines XX-XX in FIGS. 17, 18 and 19. A gray value profile 56 is produced in the reconstruction shown in FIG. 17 on the basis of mono-energetic projection images. A further gray value profile of 57 is produced on the basis of poly-energetic projection images if the correction of the beam hardening is dispensed with and a gray value profile 58 is a result of a reconstruction on the basis of poly-energetic projection images with prior correction of the beam hardening.

6.3 Empirical Modification of the Correction

The major steps of the method depicted were the pre-reconstructive component segmentation of the projection values and the determination of the material occupancies $b_W$ and $b_K$. With this the hardening-corrected projection values converted into monochromatic spectrum are then obtained according to equation (#7).

It is shown empirically that—in particular because of the difficult component segmentation—the proposed hardening correction occasionally tends to over- or undercompensation. In order to create an opportunity for modification the correction can be undertaken as additive correction with a correction component $\delta p$ corresponding to equation (#11) and this additive correction component can also be multiplied by a weighting factor $\gamma$. For undercompensation $\gamma>1$ and for overcompensation $\gamma<1$ are selected in order to minimize the residual artefacts in the reconstructed image.

Applied to equation (#11) this leads to the following modification:

$$p^{korr,\tilde{\alpha}} = \tilde{p} + \tilde{\alpha}\delta p \qquad (\#21)$$

7. Advantages

By contrast with conventional iterative correction methods no previous image reconstruction, no reprojection and no second image reconstruction is required. This means that the computing effort required is significantly lower.

By contrast with the iterative correction method, the solution described here is a direct method which is applied directly to the projection data. The correction can thus be undertaken immediately before the filtering and re-projection, so that in principle an image reconstruction keeping pace with the data acquisition is possible. In particular immediate images can be created after the end of the data acquisition.

The computing effort can be greatly reduced by the described separation. This is because the component-selective hardening correction is omitted for all projection values $p(y)$, for which the K-material proportion $p_{is\;K}(y)=0$. In the case of contrast-filled vessels this applies to the majority of the pixels.

It should be pointed out that features and properties which have been described in conjunction with a specific exemplary embodiment can also be combined with another exemplary embodiment except when this is excluded for reasons of compatibility.

Finally it is pointed out that the singular includes the plural in the claims and in the description unless the particular context indicates differently. In particular if the indefinite article is used, both the singular and also the plural are meant.

The invention claimed is:

1. A method for a beam hardening correction of a medical image of an object, comprising:
   splitting up a projection image profile of the medical image into a basic profile and a detailed profile;
   segmenting the projection image profile into a plurality of profile sections based on a predetermined feature of the detailed profile;
   assigning a first profile section to a homogeneous object area comprising a basic component of the object;
   determining a mass occupancy of the basic component in the first profile section;
   performing a one-component beam hardening correction;
   assigning a second profile section to an inhomogeneous object area comprising the basic component of the object and a detailed component of the object;
   determining the mass occupancy of the basic component and a mass occupancy of the detailed component in the second profile section based on the basic profile and the projection image profile; and
   performing a multi-component beam hardening correction.

2. The method as claimed in claim 1, wherein the object is a human being or an animal.

3. The method as claimed in claim 1, wherein the basic component comprises soft tissue.

4. The method as claimed in claim 1, wherein the detailed component comprises bone or an implant.

5. The method as claimed in claim 1, wherein the mass occupancy of the basic component is determined based on the basic profile and the mass occupancy of the detailed component is determined based on the projection image profile.

6. The method as claimed in claim 5, wherein the detailed component comprises soft tissue filed with a contrast media.

7. The method as claimed in claim 1, wherein a total mass occupancy of the basic component and the detailed component is determined from the basic profile and the mass occupancy of the detailed component is determined from the projection image profile.

8. The method as claimed in claim 1, wherein the basic profile is determined by adapting an adaptation curve to the projection image profile.

9. The method as claimed in claim 1, wherein the detailed profile is determined by identifying a difference between the basic profile and the projection image profile.

10. The method as claimed in claim 1, wherein the second profile section is defined by a threshold value criterion.

11. The method as claimed in claim 1, wherein the projection image profile is formed along a row of detector elements of an x-ray detector.

12. A device for recording a medical image of an object, comprising:
   a radiation source that emits radiations to the object;
   a radiation detector that records the medical image by detecting the radiations passing through the object; and
   an evaluation unit connected to the radiation detector that:
     splits up a projection image profile of the medical image into a basic profile and a detailed profile,
     segments the projection image profile into a plurality of profile sections based on predetermined features of the detailed profile,
     assigns a first profile section to a homogeneous object area comprising a basic component of the object,
     determines a mass occupancy of the basic component in the first profile section,
     performs a one-component beam hardening correction,
     assigns a second profile section to an object area comprising the basic component and a detailed component of the object,
     determines the mass occupancy of the basic component and a mass occupancy of the detailed component in the second profile section based on the basic profile and the projection image profile, and
     performs a multi-component beam hardening correction.

13. The device as claimed in claim 12, wherein the radiation detector and the radiation source are moved on opposite sides around the object.

14. The device as claimed in claim 12, wherein the device is an x-ray device.

15. The device as claimed in claim 12, wherein the basic profile is determined by adapting an adaptation curve to the projection image profile.

16. The device as claimed in claim 12, wherein the detailed profile is determined by identifying a difference between the basic profile and the projection image profile.

17. The device as claimed in claim 12, wherein the mass occupancy of the basic component is determined based on the basic profile and the mass occupancy of the detailed component is determined based on the projection image profile.

18. The device as claimed in claim 12, wherein a total mass occupancy of the basic component and the detailed component is determined from the basic profile and the mass occupancy of the detailed component is determined from the projection image profile.

19. The device as claimed in claim 12, wherein the basic component comprises soft tissue.

20. The device as claimed in claim 12, wherein the detailed component comprises bone or an implant.

* * * * *